(12) United States Patent
Wesley

(10) Patent No.: US 9,364,252 B2
(45) Date of Patent: *Jun. 14, 2016

(54) HAIR RESTORATION SURGERY

(75) Inventor: Carlos K. Wesley, New York, NY (US)

(73) Assignee: PiloFocus, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/496,905

(22) PCT Filed: Sep. 17, 2010

(86) PCT No.: PCT/US2010/049283
§ 371 (c)(1),
(2), (4) Date: Apr. 30, 2012

(87) PCT Pub. No.: WO2011/035125
PCT Pub. Date: Mar. 24, 2011

(65) Prior Publication Data
US 2012/0215231 A1 Aug. 23, 2012

Related U.S. Application Data

(60) Provisional application No. 61/243,271, filed on Sep. 17, 2009.

(51) Int. Cl.
*A61B 17/50* (2006.01)
*A61B 17/3205* (2006.01)
(Continued)

(52) U.S. Cl.
CPC ....... *A61B 17/32053* (2013.01); *A61B 1/00087* (2013.01); *A61B 17/32002* (2013.01);
(Continued)

(58) Field of Classification Search
CPC ............. A61B 2017/00752; A61B 17/3209; A61B 1/00101; A61B 2017/00296; A61B 2010/0258; A61B 10/0241; A61B 10/025; A61B 10/0275; A61B 10/0283; A61B 2017/320024; A61B 2017/320028; A61B 2017/320032; A61B 2017/320056; A61B 2017/320052; A61B 2017/320076; A61B 2017/320064; A61B 2017/32004; A61B 17/320016; A61B 17/32002; A61B 17/32093; A61B 2010/0208; A61B 10/0266; A61B 10/0233; A61B 10/02; A61B 2018/00476; A61B 2017/00747; A45D 26/00; A45D 26/0057; A45D 26/0023; A45D 26/0038; A45D 2026/008; A45D 26/0028; A61F 2/10
USPC ............ 606/133, 46, 159, 131, 187; 600/564, 600/565, 566, 567
See application file for complete search history.

(56) References Cited

U.S. PATENT DOCUMENTS 4,476,864 A 10/1984 Tezel
4,763,669 A * 8/1988 Jaeger ........................... 600/564
(Continued)

FOREIGN PATENT DOCUMENTS

EP 1642541 A1 4/2006
GB 2021467 A 12/1979
(Continued)

OTHER PUBLICATIONS

Invitation to Pay Additional Fees and, Where Applicable, Protest Fee for corresponding International Application No. PCT/US2014/037358, dated Sep. 4, 2014 (6 pages).
International Search Report and Written Opinion for corresponding International Application No. PCT/US2014/037358, dated Oct. 27, 2014 (15 pages).
(Continued)

*Primary Examiner* — Tuan V Nguyen
*Assistant Examiner* — Chima Igboko
(74) *Attorney, Agent, or Firm* — Brinks Gilson & Lione; Craig Buschmann; Ryan L. Marshall

(57) ABSTRACT

A surgical apparatus includes an elongated member (1), a dissection module (10), and an extraction module (701). The dissection module is removably attachable to a first end of the elongated member and includes a tissue separating device (10). The extraction module is removably attachable to the first end of the elongated member and includes a suction port and a tissue removal implement (13,14) disposed within the suction port.

24 Claims, 15 Drawing Sheets

(51) Int. Cl.
*A61B 1/00* (2006.01)
*A61B 17/32* (2006.01)
A61B 17/3209 (2006.01)
A61B 17/00 (2006.01)
A61B 17/30 (2006.01)
A61F 2/10 (2006.01)

(52) U.S. Cl.
CPC . *A61B17/32093* (2013.01); *A61B 2017/00296* (2013.01); *A61B 2017/00752* (2013.01); *A61B 2017/306* (2013.01); *A61F 2/10* (2013.01)

(56) References Cited

U.S. PATENT DOCUMENTS

| | | | |
|---|---|---|---|
| 5,133,360 A * | 7/1992 | Spears | 600/567 |
| 5,133,722 A * | 7/1992 | Avrahami et al. | 606/133 |
| 5,135,531 A * | 8/1992 | Shiber | 606/159 |
| 5,368,014 A | 11/1994 | Anapliotis et al. | |
| 5,391,166 A | 2/1995 | Eggers | |
| 5,439,475 A | 8/1995 | Bennett | |
| 5,445,615 A | 8/1995 | Yoon | |
| 5,472,439 A | 12/1995 | Hurd | |
| 5,478,351 A | 12/1995 | Meade et al. | |
| 5,535,759 A | 7/1996 | Wilk | |
| 5,601,601 A | 2/1997 | Tal et al. | |
| 5,618,303 A | 4/1997 | Marlow et al. | |
| 5,630,782 A | 5/1997 | Adair | |
| 5,665,100 A * | 9/1997 | Yoon | 606/170 |
| 5,676,678 A | 10/1997 | Schad | |
| 5,676,680 A | 10/1997 | Lim | |
| 5,782,851 A | 7/1998 | Rassman | |
| 5,782,853 A | 7/1998 | Zeevi | |
| 5,788,651 A | 8/1998 | Weilandt | |
| 5,792,163 A | 8/1998 | Hitzig | |
| 5,817,120 A | 10/1998 | Rassman | |
| 5,823,971 A * | 10/1998 | Robinson et al. | 600/567 |
| 5,827,297 A | 10/1998 | Boudjema | |
| 5,895,403 A | 4/1999 | Collinsworth | |
| 5,922,000 A | 7/1999 | Chodorow | |
| 5,984,936 A | 11/1999 | Mangubat | |
| 6,027,512 A | 2/2000 | Bridges | |
| 6,059,719 A * | 5/2000 | Yamamoto et al. | 600/127 |
| 6,352,503 B1 * | 3/2002 | Matsui et al. | 600/104 |
| 6,419,627 B1 | 7/2002 | Ben Nun | |
| 6,500,170 B2 | 12/2002 | Palmer et al. | |
| 6,544,259 B1 | 4/2003 | Tsaliovich | |
| 6,572,625 B1 * | 6/2003 | Rassman | 606/133 |
| 6,585,746 B2 | 7/2003 | Gildenberg | |
| 6,620,158 B2 * | 9/2003 | Ronci | 606/36 |
| 7,130,717 B2 | 10/2006 | Gildenberg | |
| 7,156,856 B2 | 1/2007 | Feller | |
| 7,261,721 B2 | 8/2007 | Feller | |
| 7,329,252 B1 * | 2/2008 | Yamazaki et al. | 606/9 |
| 7,517,321 B2 | 4/2009 | McCullough et al. | |
| 7,621,933 B2 | 11/2009 | Bodduluri | |
| 7,621,934 B2 | 11/2009 | Bodduluri | |
| 7,627,157 B2 | 12/2009 | Qureshi | |
| 7,727,164 B2 | 6/2010 | Cicenas et al. | |
| 7,806,121 B2 | 10/2010 | Bodduluri | |
| RE42,381 E | 5/2011 | Gildenberg | |
| RE42,437 E | 6/2011 | Gildenberg | |
| RE42,438 E * | 6/2011 | Gildenberg | 700/245 |
| 7,962,192 B2 | 6/2011 | Bodduluri | |
| 8,048,090 B2 | 11/2011 | Qureshi | |
| 8,066,717 B2 | 11/2011 | DuBois | |
| 8,104,480 B2 | 1/2012 | Bodduluri | |
| 8,128,639 B2 | 3/2012 | Tippett | |
| 8,133,237 B2 | 3/2012 | Oostman, Jr. | |
| 8,133,247 B2 | 3/2012 | Bodduluri | |
| 8,317,804 B1 * | 11/2012 | Rassman et al. | 606/133 |
| 8,454,627 B2 | 6/2013 | Bodduluri et al. | |
| 8,690,894 B2 | 4/2014 | Bodduluri et al. | |
| 8,998,931 B2 | 4/2015 | Wesley et al. | |
| 2002/0042623 A1 | 4/2002 | Blatter et al. | |
| 2002/0103500 A1 * | 8/2002 | Gildenberg | 606/187 |
| 2003/0040706 A1 | 2/2003 | Kuracina et al. | |
| 2003/0097143 A1 * | 5/2003 | Mittelstaedt | 606/172 |
| 2003/0097144 A1 | 5/2003 | Lee | |
| 2003/0120298 A1 * | 6/2003 | Gildenberg | 606/187 |
| 2003/0212415 A1 | 11/2003 | Karasiuk | |
| 2003/0233114 A1 | 12/2003 | Merboth et al. | |
| 2004/0049206 A1 | 3/2004 | Rassman | |
| 2004/0092924 A1 | 5/2004 | Vasa | |
| 2004/0097973 A1 | 5/2004 | Loshakove et al. | |
| 2005/0049622 A1 * | 3/2005 | Mittelstaeot | 606/167 |
| 2005/0177142 A1 * | 8/2005 | Jay | 606/9 |
| 2005/0216035 A1 * | 9/2005 | Kraus et al. | 606/133 |
| 2005/0267506 A1 | 12/2005 | Harris | |
| 2006/0142741 A1 * | 6/2006 | Jay | 606/3 |
| 2006/0161179 A1 | 7/2006 | Kachenmeister | |
| 2006/0178677 A1 * | 8/2006 | Brinson | 606/133 |
| 2006/0200040 A1 | 9/2006 | Weikel et al. | |
| 2006/0259102 A1 * | 11/2006 | Slatkine | 607/88 |
| 2007/0078466 A1 | 4/2007 | Bodduluri | |
| 2007/0078473 A1 | 4/2007 | Bodduluri et al. | |
| 2007/0106307 A1 | 5/2007 | Bodduluri | |
| 2007/0122387 A1 | 5/2007 | Cochran | |
| 2007/0128172 A1 | 6/2007 | Yoshizato | |
| 2007/0156164 A1 | 7/2007 | Cole | |
| 2007/0213741 A1 | 9/2007 | Cole | |
| 2007/0255293 A1 | 11/2007 | Corre | |
| 2007/0293884 A9 * | 12/2007 | Cole et al. | 606/187 |
| 2008/0033410 A1 | 2/2008 | Rastegar et al. | |
| 2008/0033455 A1 * | 2/2008 | Rassman et al. | 606/133 |
| 2008/0051805 A1 * | 2/2008 | Pinchuk | 606/133 |
| 2008/0051806 A1 * | 2/2008 | Cole | 606/133 |
| 2008/0091225 A1 * | 4/2008 | Cole et al. | 606/172 |
| 2008/0097458 A1 | 4/2008 | Donahoe et al. | |
| 2008/0177287 A1 * | 7/2008 | Rassman et al. | 606/133 |
| 2008/0186496 A1 | 8/2008 | Leveque | |
| 2008/0200861 A1 | 8/2008 | Shalev et al. | |
| 2008/0215039 A1 * | 9/2008 | Slatkine et al. | 606/9 |
| 2008/0234697 A1 | 9/2008 | DuBois | |
| 2008/0234698 A1 | 9/2008 | Oostman | |
| 2009/0005765 A1 | 1/2009 | Oostman, Jr. | |
| 2009/0012536 A1 | 1/2009 | Rassman et al. | |
| 2009/0052738 A1 | 2/2009 | Qureshi | |
| 2009/0088776 A1 | 4/2009 | Harris | |
| 2009/0240261 A1 | 9/2009 | Drews | |
| 2009/0306498 A1 | 12/2009 | Bodduluri | |
| 2009/0306680 A1 | 12/2009 | Qureshi | |
| 2010/0080415 A1 | 4/2010 | Qureshi | |
| 2010/0080417 A1 | 4/2010 | Qureshi | |
| 2010/0082042 A1 | 4/2010 | Drews | |
| 2010/0125287 A1 | 5/2010 | Cole | |
| 2010/0166719 A1 | 7/2010 | Yoshizato | |
| 2010/0217236 A1 | 8/2010 | Gill | |
| 2010/0262129 A1 | 10/2010 | Roy | |
| 2011/0046639 A1 | 2/2011 | Giotis | |
| 2011/0060321 A1 | 3/2011 | Chandler | |
| 2011/0160746 A1 | 6/2011 | Umar | |
| 2011/0178533 A1 | 7/2011 | Oostman, Jr. | |
| 2011/0224693 A1 | 9/2011 | Bodduluri | |
| 2011/0245845 A1 | 10/2011 | Oostman, Jr. | |
| 2011/0319921 A1 | 12/2011 | Giotis | |
| 2012/0010631 A1 | 1/2012 | DuBois | |
| 2012/0039516 A1 | 2/2012 | Qureshi | |
| 2012/0041430 A1 | 2/2012 | Anderson | |
| 2012/0041451 A1 | 2/2012 | Bodduluri | |
| 2013/0190776 A1 | 7/2013 | Zhang et al. | |
| 2013/0226213 A1 | 8/2013 | Kim et al. | |
| 2013/0304090 A1 | 11/2013 | Oostman et al. | |
| 2014/0243870 A1 | 8/2014 | Wesley et al. | |

FOREIGN PATENT DOCUMENTS

| | | |
|---|---|---|
| JP | 59-114511 | 7/1984 |
| JP | 64-080335 | 3/1989 |
| JP | 03-086315 | 4/1991 |
| JP | 09-215656 | 8/1997 |
| JP | 2000-014631 | 1/2000 |
| JP | 2000-037348 | 2/2000 |
| JP | 2001-511393 | 8/2001 |

(56) References Cited

FOREIGN PATENT DOCUMENTS

| | | |
|---|---|---|
| JP | 2008-502437 | 1/2006 |
| JP | 2011-516169 A | 5/2011 |
| KR | 2007-0037577 A | 4/2007 |
| WO | WO99/05997 | 2/1999 |
| WO | WO 01/35125 A1 | 5/2001 |
| WO | WO2005109799 A2 | 11/2005 |
| WO | WO2007041267 A2 | 4/2007 |
| WO | WO2007087463 A2 | 8/2007 |
| WO | WO2008024954 A2 | 2/2008 |
| WO | WO 2008/027829 A2 | 3/2008 |
| WO | WO2009083741 A1 | 7/2009 |
| WO | WO2009123635 A1 | 10/2009 |
| WO | WO2010039413 A1 | 4/2010 |
| WO | WO2010041089 A1 | 4/2010 |
| WO | WO2010057018 A2 | 5/2010 |
| WO | WO2010131270 A1 | 11/2010 |
| WO | WO2011035125 A1 | 3/2011 |
| WO | WO2011082130 A2 | 7/2011 |
| WO | WO2011123218 A1 | 10/2011 |
| WO | WO 2013/059349 A1 | 4/2013 |
| WO | WO 2014/182941 A1 | 11/2014 |

OTHER PUBLICATIONS

English translation of JP Office Action entered on Apr. 15, 2014 in corresponding JP Pat. App. No. 2012-529930.
English translation of CN Office Action entered on Apr. 11, 2014 in corresponding CN Pat. App. No. 201080052239.3.
International Preliminary Report on Patentability for International Application No. PCT/US2012/060653, dated Apr. 22, 2014 (8 pages).
Patent Examination Report No. 1 for Australian Application No. 2014203223, dated Apr. 30, 2015 (3 pages).
Second Office Action for corresponding Chinese Application No. 201080052239.3, dated Nov. 19, 2014 (15 pages).
Office Action with English translation for related South Korean Application No. 10-2012-7009817, dated Dec. 14, 2015 (13 pages).
Third Office Action, and English language translation thereof, in Chinese Application No. 201080052239.3, dated Jul. 1, 2015, 17 pages.
Notification of Reasons for Rejection with English translation for related Japanese Application No. 2014-537187, dated Jan. 5, 2016 (4 pages).

* cited by examiner

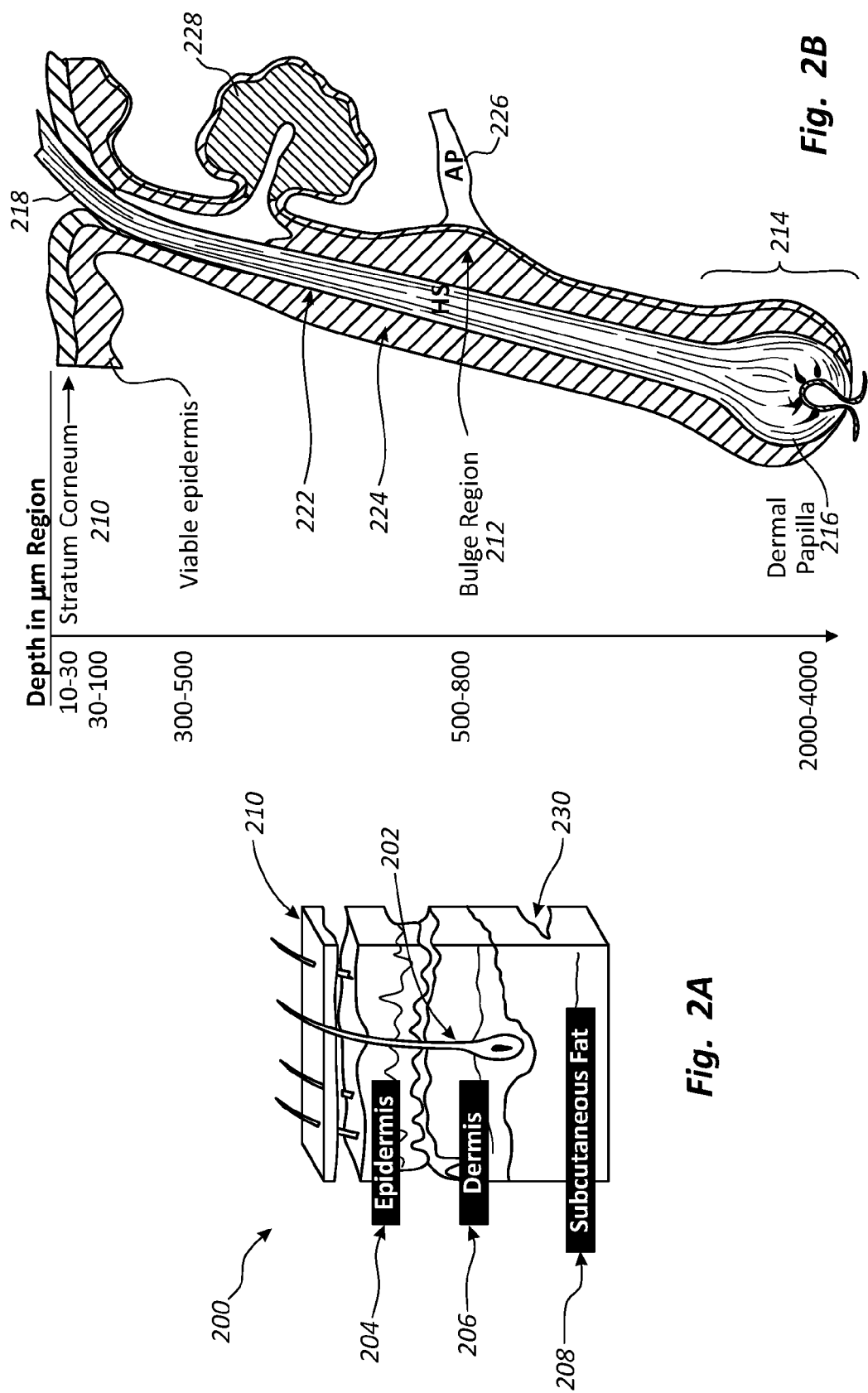

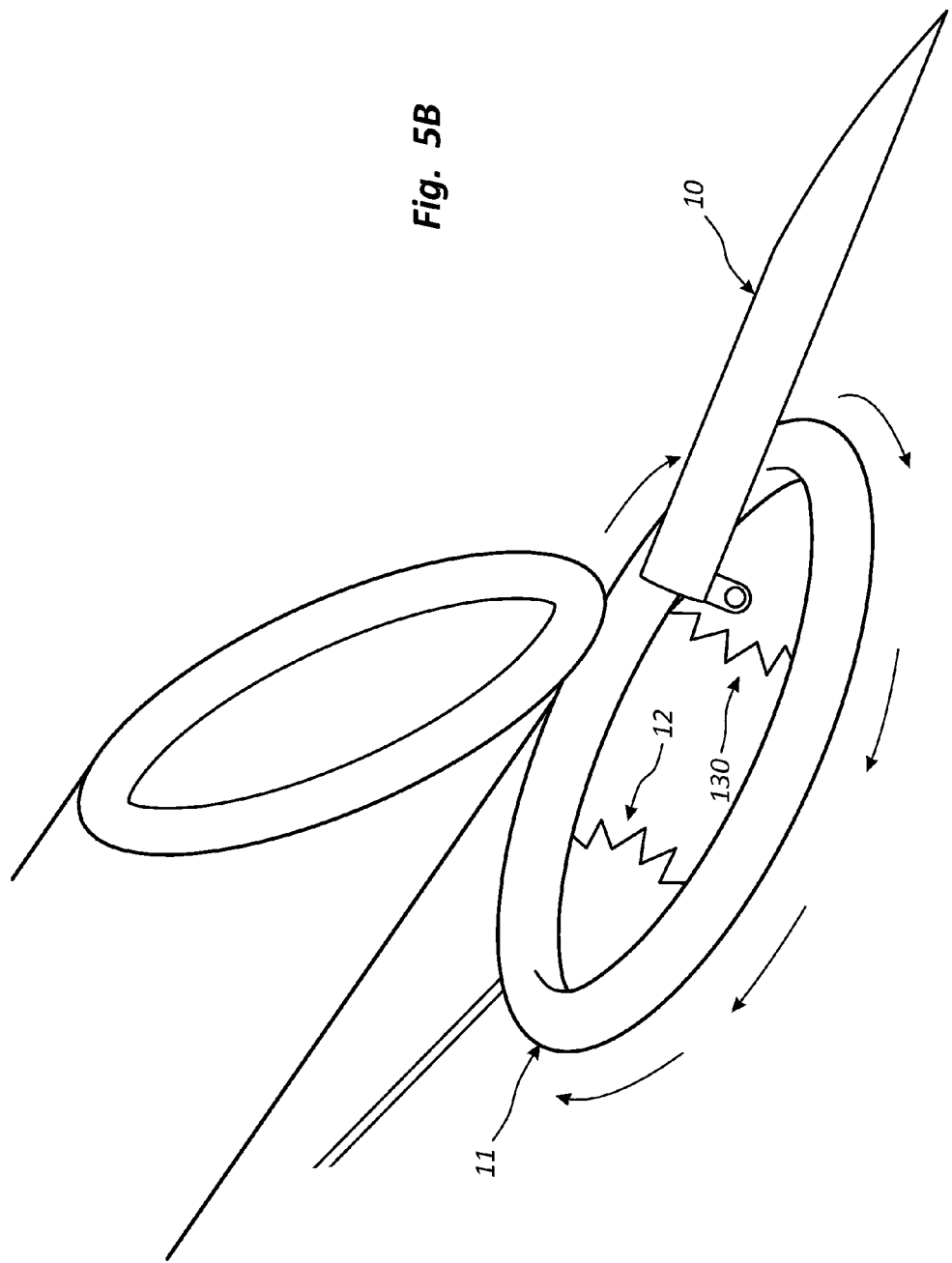

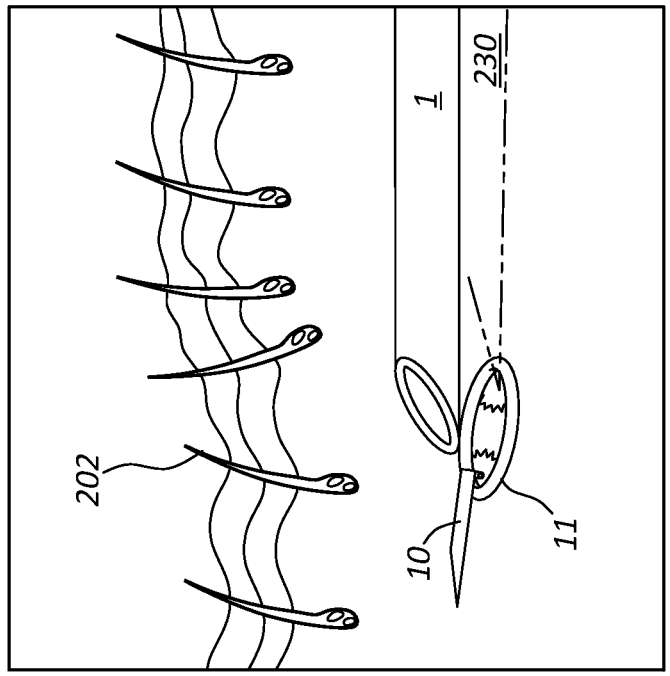
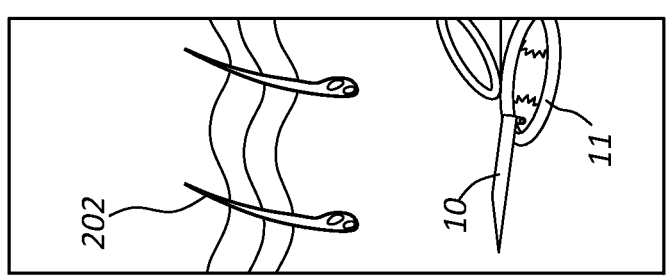
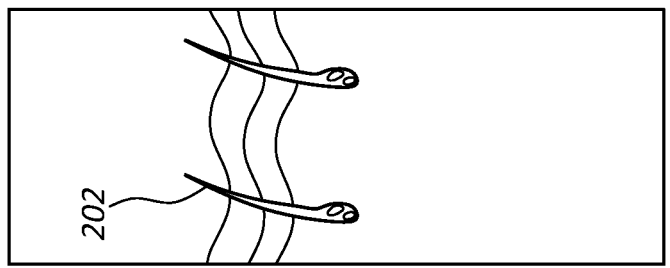
Fig. 5E
Fig. 5D
Fig. 5C

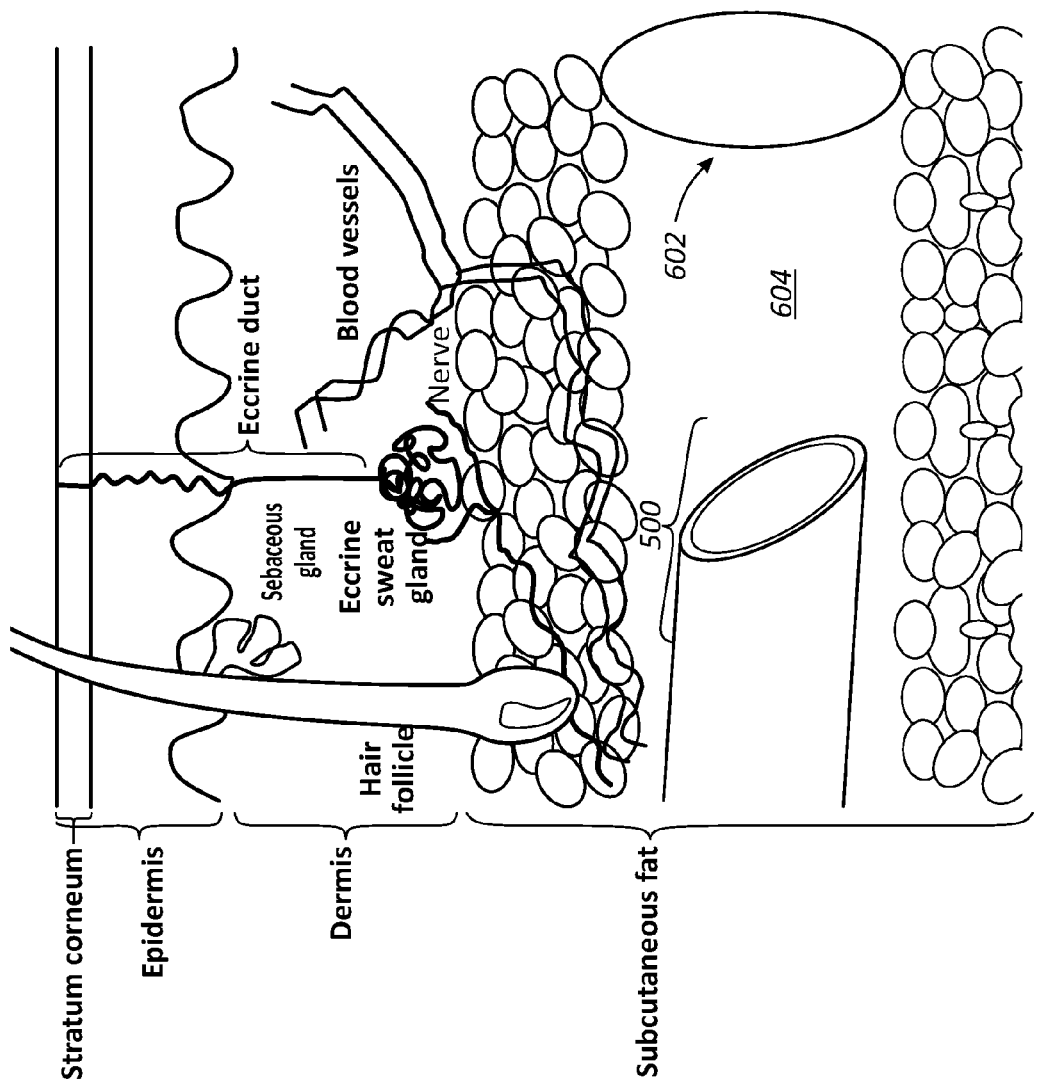

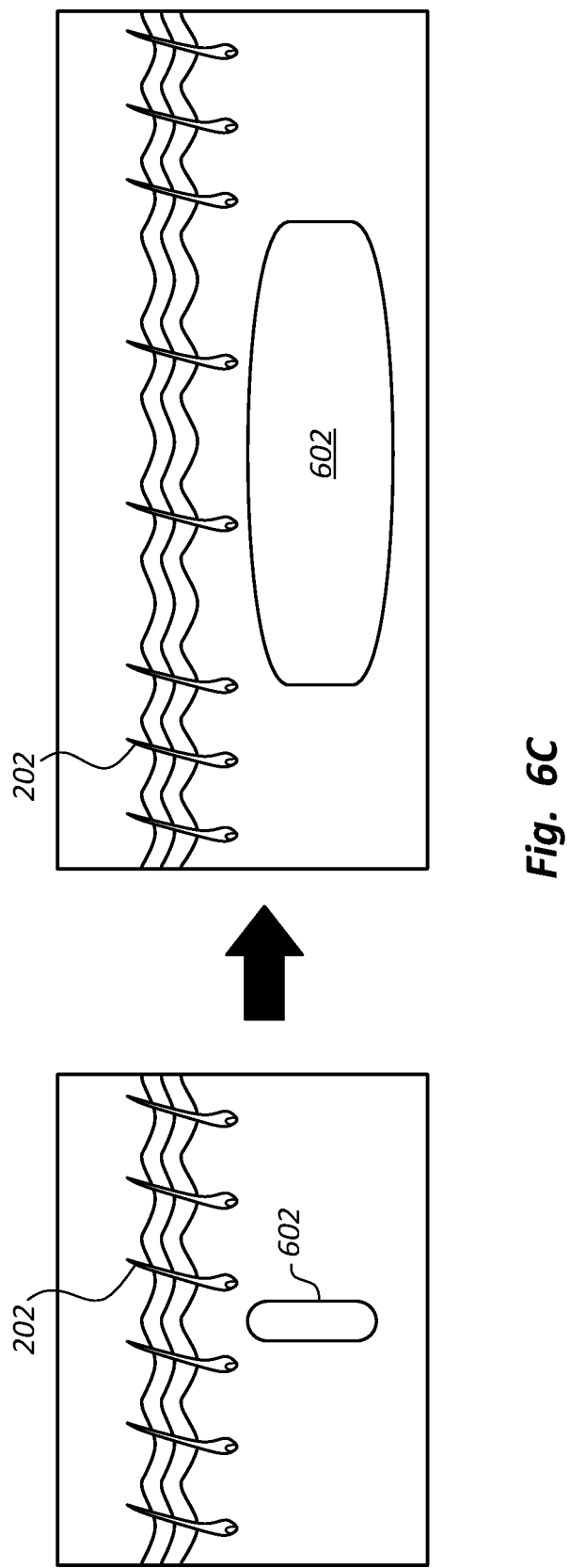

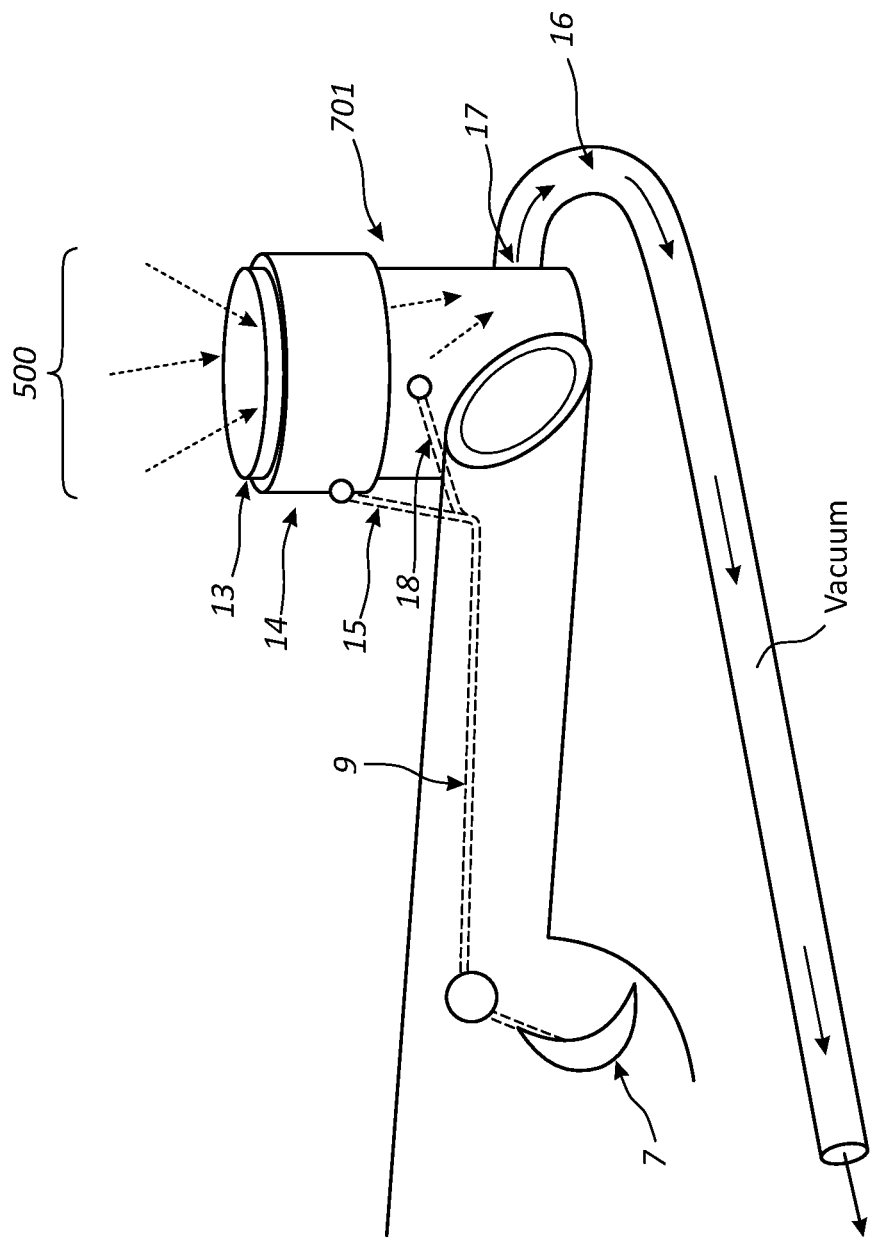

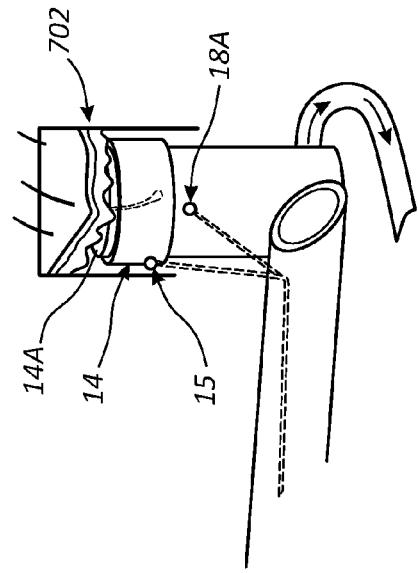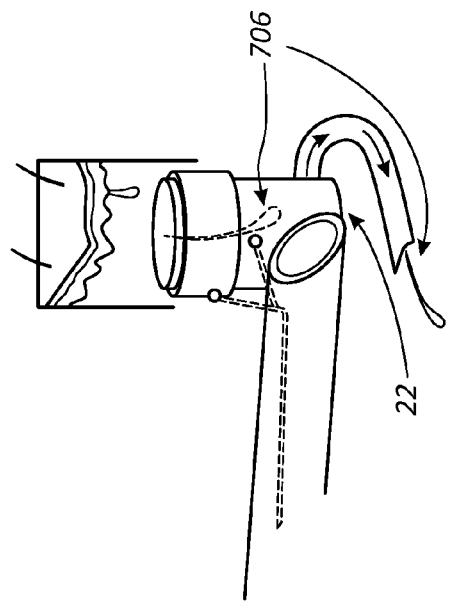
Fig. 7A
Fig. 7B
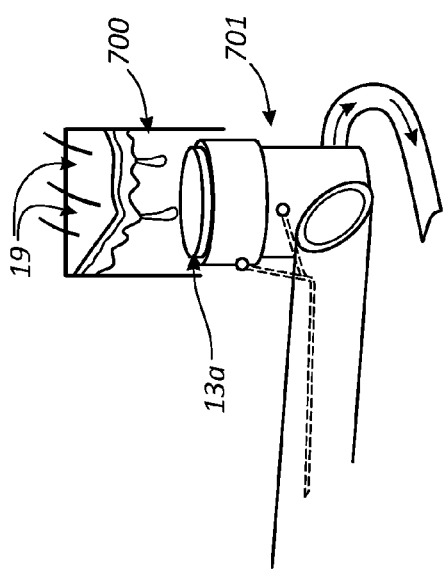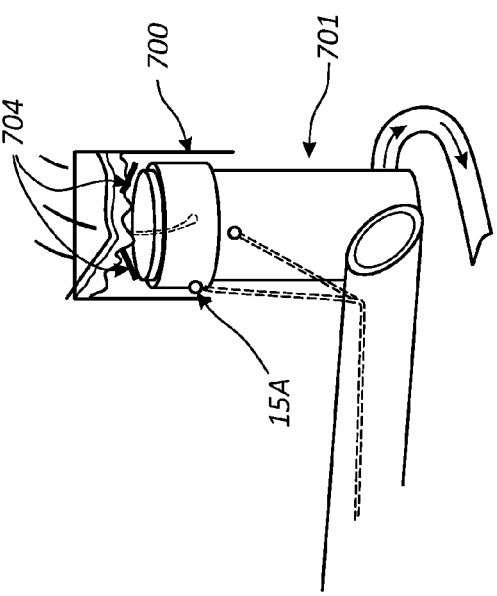
Fig. 7C
Fig. 7D

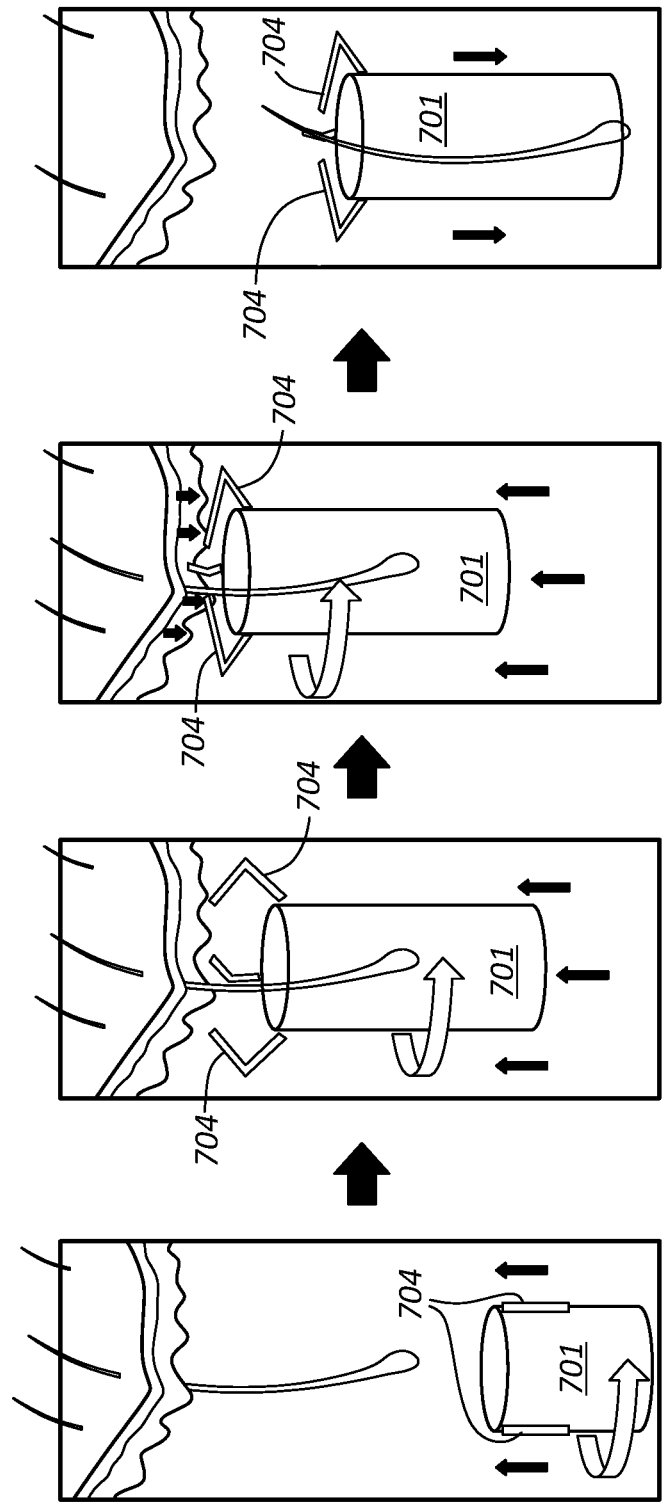

HAIR RESTORATION SURGERY

CROSS REFERENCE TO RELATED APPLICATIONS

This application is a National Stage of International Application No. PCT/US10/49283, filed on Sep. 17, 2010, which claims priority to U.S. Provisional Application No. 61/243,271 filed Sep. 17, 2009. The content of the prior applications are incorporated herein by reference in their entirety.

FIELD OF THE INVENTION

This invention relates to hair restoration.

BACKGROUND

The surgical method of donor removal in Hair Restoration Surgery (HRS) rests on the principal of "donor dominance": the idea that hair from the "donor area", the region of the scalp in which the hair is destined to remain, will continue to grow in the same fashion even when transplanted to the "recipient area", the scalp zone of non-permanent hair growth.

Beginning around the 1950s, large punch grafts were excised from the donor area and transplanted to the recipient area. Utilization of these large grafts was necessary to ensure hair survival after transplantation. Smaller grafts, or implantation into smaller recipient sites, were not yet feasible due to the low graft viability secondary to decreased blood perfusion of transplanted grafts. While this large-graft method enabled transplanted graft growth in the recipient area, the grafts often had a "pluggy" appearance and the punched-out scars in the donor area left an unattractive buckshot pattern in the back of a patient's head.

To address these shortcomings of original HRS techniques, an alternative to donor hair harvesting in the form of a strip technique was proposed. This approach involved removing a strip of hair-follicle bearing skin from the donor region, suturing the donor wound closed, dissecting out each individual follicle or cluster of follicles (a.k.a. follicular unit (FU)), and transplanting each individual FU separately in the recipient area. This approach, coined "micrografting" or follicular unit transplanting (FUT), helped minimize the "pluggy" appearance of large grafts in the recipient area and left only a linear scar in the donor area rather than a more-obvious buckshot pattern.

Motivated by a desire to obtain the largest number of grafts via the "micrografting" technique, many patients pushed for wider donor strip removal and were subsequently left with relatively large (2-10 mm) linear scars in the occipital (back) portion of their head. This obvious telltale sign of the surgery provided impetus for the development of follicular unit extraction (FUE). In FUE each individual follicular unit is meticulously punched out from the donor area with a small biopsy punch and transplanted into the recipient area. This differs from the original approach to HRS in that FUE involves the transfer of only individual FUs rather than large (4-5 mm) punch grafts. This novel technique eliminated the stigma of a linear scar in the donor area and, when done properly, minimized the appearance of a buckshot pattern in the donor area. However, several disadvantages persisted with the advent of FUE: a high percentage (up to 40%) of hairs are transected (thus, limiting their survival), a moth-eaten scarring pattern often remains from where FUs are extracted, and a considerable number of patients (up to 30%) are not candidates for FUE based on their hair characteristics (e.g. light color or considerable curl) that present undue challenges for the surgeon.

SUMMARY

In a general aspect, a surgical apparatus includes an elongated member, a dissection module, and an extraction module. The dissection module is removably attachable to a first end of the elongated member and includes a tissue separating device. The extraction module is removably attachable to the first end of the elongated member and includes a suction port and a tissue removal implement disposed within the suction port.

Embodiments may include one or more of the following. The apparatus accepts the first module or the second module interchangeably. The apparatus includes an imaging system attached to a second end of the elongated member, the imaging system including a light source for illuminating a target through a hollow passage in the elongated member between the first end and the second end; and a viewing port for receiving an image of the target.

The tissue removal implement is disposed concentrically within the suction port. The tissue removal implement is hollow. The tissue removal implement is substantially cylindrical. The tissue removal implement is configured to separate the target region of tissue from surrounding tissue. The tissue removal implement includes a plurality of curved cutting devices disposed around a most superficial border of the tissue removal implement. The cutting devices include at least one of sharp blades, blunt blades, arms, levers, chemicals, enzymes, or lasers.

The tissue removal implement is configured to be operated by an operator. The tissue removal implement is configured for automatic operation. The tissue removal implement includes a plurality of gripping ledges disposed on an inner surface of the tissue removal implement.

The suction port is configured to apply suction to a target region of tissue. The suction port is oriented substantially at an angle to a longitudinal axis of the elongated member. The suction port is in fluid communication with a reservoir that receives a region of tissue extracted by the tissue removal implement.

The elongated member includes a control mechanism connectable to the tissue separating device or the tissue removal implement. The tissue separating device is configured to move relative to the elongated member. The extraction module further comprises a sensor configured to detect a structure of the skin.

The target region of tissue includes a hair follicle. The elongated member is rigid or flexible. The tissue separating device includes at least one of a sharp blade, a blunt blade, a balloon, an electrocautery device, a device that dispenses a pressurized gas or liquid, a laser, and an enzymatic or chemical tissue separator.

In another general aspect, an endoscopic surgery kit includes a dissection device for dissecting a cavity below the skin of a patient and an extraction device for insertion into the cavity. The dissection device includes a first elongated member and a tissue separating device attached to a first end of the first elongated member. The extraction device includes a second elongated member, a suction port attached to a first end of the second elongated member, and a tissue removal implement disposed within the suction port.

Embodiments may include one or more of the following. The dissection device includes an imaging system positioned at a second end of the first elongated member. The imaging system includes a light source for illuminating a target located at the first end of the first elongated member through a hollow passage in the first elongated member and a viewing port for receiving an image of the target. The extraction device includes an imaging system positioned at a second end of the second elongated member.

The tissue removal implement is disposed concentrically within the suction port. The suction port is oriented at an angle to a longitudinal axis of the second elongated member.

The endoscopic surgery kit further includes a barrier device configured to be positioned within the cavity and to restrict the operation of the extraction device to a region defined by the barrier device. The barrier device is configured to maintain the cavity open. The region defined by the barrier device is determined on the basis of a characteristic of the patient.

The endoscopic surgery kit further includes a reservoir in fluid communication with the suction port.

In a further aspect, a method includes using a tissue separating device attached to an end of an elongated member, creating a cavity below the skin of a patient and, from the cavity, applying suction to a selected portion of skin tissue superficial to the cavity via a suction port attached to the end of the elongated member; isolating the selected portion of skin tissue from surrounding tissue using a tissue removal implement disposed within the suction port; and applying a downward force to the selected portion of skin tissue using the tissue removal implement to extract the selected portion of skin tissue from the surrounding tissue without altering an outward appearance of the skin.

Embodiments may include one or more of the following. The selected portion of skin tissue includes a hair follicle and creating a cavity below the skin includes creating a cavity in a plane below the hair follicles.

The elongated member is an endoscope. The method further includes selecting the selected portion of skin tissue on the basis of an image obtained through the endoscope. The method further includes obtaining an image of the selected portion of skin tissue. The image is obtained from within the cavity.

Applying the downward force includes rotating the tissue removal implement. The method includes detecting a position of the tissue removal implement relative to an outer surface of the skin.

The method further includes positioning a barrier device within the cavity. The barrier device is configured to restrict the operation of the tissue removal implement to a region defined by the barrier device. The barrier device is configured to maintain the cavity open. The method further includes determining the region defined by the barrier device on the basis of a characteristic of the patient.

The method includes storing the extracted tissue in a reservoir.

In a further general aspect, a method includes creating a cavity below the skin using a tissue separating device attached to the end of an elongated member. The method further includes, from the cavity, performing a tissue alteration procedure on a selected portion of skin tissue superficial to the cavity using a tissue alteration implement attached to the end of the elongated member without altering an outward appearance of the skin.

Embodiments may include one or more of the following. The selected portion of skin tissue includes a hair follicle. The tissue alteration procedure includes at least one of irradiation with a laser, cautery, tissue structural alteration, biochemical alteration, application of heat, application of electric current, or application of enzymes. The tissue alteration procedure includes removal, ablation, or destruction of the selected portion of skin tissue.

An endoscopic approach to hair restoration as described herein has a number of advantages. Post-surgical scarring in the donor area is minimized or eliminated because the follicles are approached from beneath the surface of the skin and subsequent FU removal leaves an intact stratum corneum. Eliminating the large, linear, full-thickness scalp incisions as well as the subsequent tension placed on wound edges upon donor region closure also makes painful, aching, and sharp neuropathic pain from nerve trauma virtually non-existent. These two advantages contribute to the shortened post-operative recovery time required for HRS patients who undergo endoscopic HRS, or piloscopy.

Visualizing the incorporation of the stem-cell containing components of the follicle necessary for self-renewal (e.g. the bulge within the isthmus, the bulb containing dermal papilla, etc.) ensures that no FU are transected as they are removed from the donor area. As such, piloscopy allows for nearly 100% graft viability when each FU is transplanted to the recipient area.

Furthermore, since an endoscopic approach to follicular extraction leaves no question as to whether the components for follicular self renewal are included with each extraction of donor FU, restrictions on eligible patient population are lifted. This, in turn, expands the patient population who can benefit from the surgery.

BRIEF DESCRIPTION OF DRAWINGS

FIG. 2A is a cross-section of the layers of skin and hair.

FIG. 2B is a detailed depiction of an intact hair follicle.

FIG. 5B shows a magnified view of the dissection blade attachment of the endoscope of FIG. 5A.

FIGS. 5C-5E depict the steps by which the dissection blade creates the visual cavity.

FIG. 6A shows a cross section of the visual cavity maintained by a barrier device

FIG. 6C depicts how the barrier device of FIG. 6A increases the distance between each hair follicle.

FIG. 7 shows an endoscope with an extraction device attachment.

FIGS. 7A-7D illustrate steps in the use of the extraction device of FIG. 7.

FIGS. 7E-7H illustrate the manner in which the extraction device extracts a hair follicle.

DETAILED DESCRIPTION

Figure 1A:
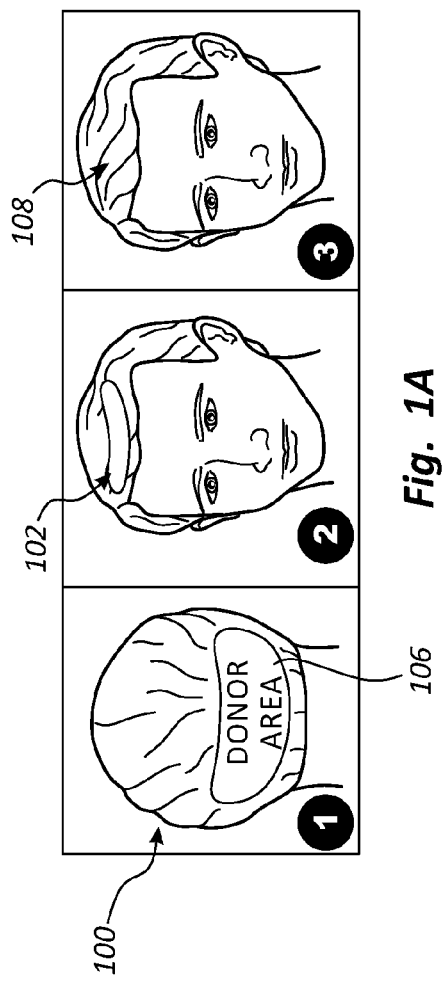
FIGS. 1A and 1B illustrate the principle of hair restoration surgery.
Figure 1B:
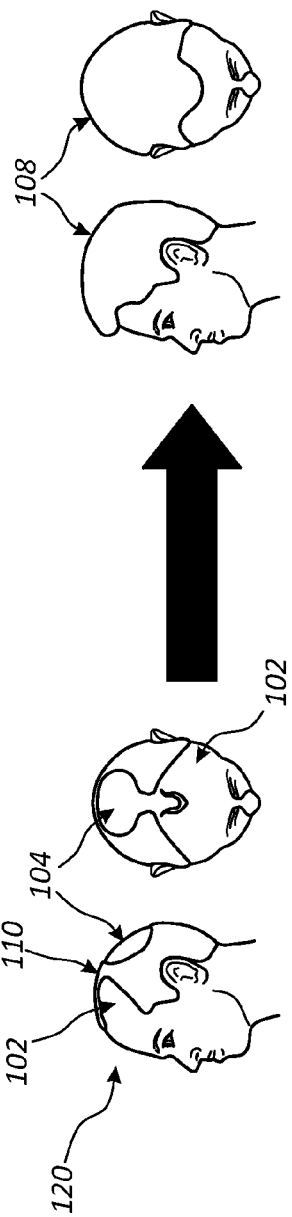

Referring to FIGS. 1A and 1B, a patient 100, 120 experiences hair loss in patterns consistent with androgenetic alopecia (male pattern baldness or female pattern hair loss) or in more random (focal or diffuse) patterns as seen from various non-androgenetic pathologies such as cicatricial alopecia. The most commonly-affected areas in androgenetic alopecia are a frontal third 102, a midscalp 110, and a vertex (or crown) 104. Surgical hair restoration harvests hair follicles from a donor area 106 and transplants the intact follicles to the desired regions of hair loss which include, but are not limited to, regions 102, 110, and 104. After full growth of the transplanted follicles has been achieved, the post-operative patient enjoys a fuller head of hair 108, thicker eyebrows, fuller eyelashes, or even more substantial facial or body hair. In endoscopic surgical hair restoration, or piloscopy, individual intact hair follicles are removed with minimal or no disruption of the stratum corneum 210 (i.e., the skin surface; see FIG. 2A) by an endoscopic device inserted beneath the scalp.

Referring to FIGS. 2A and 2B, a cross-section of skin 200 shows the native tissue surrounding a hair follicle 202. Spanning three separate layers of the skin (an epidermis 204, a dermis 206, and a fat-containing, subcutaneous layer 208) the follicle 202 protrudes through the skin surface at the most superficial layer of the epidermis 204, called the stratum corneum 210. The intact hair follicle 202 is depicted in detail in FIG. 2B and includes the components that enable self-renewal of the follicle after it is transplanted into viable autologous tissue. The two critical regions in which stem cells abound are a bulge region 212 located near an erector pilli muscle 226 and a follicular bulb 214 which contains a dermal papilla 216. Communication between these two stem-cell enriched areas promotes hair follicle regeneration. Other components of an intact hair follicle 202 include a hair shaft 218, an inner root sheath 222, an outer root sheath 224, and a sebaceous gland 228.

In endoscopic surgical hair restoration, or piloscopy, each hair follicle 202 is approached and removed from beneath the surface of the skin. Specifically, each individual follicle is visualized from a uniform plane 230 that is surgically created within the subcutaneous layer 208 about 1-5 mm deep to the follicular bulbs 214 and is then excised with a small punch blade, as discussed in greater detail below. Excision incorporates a 1-7 mm portion of peri-follicular subcutaneous tissue deep to the follicular bulb 214 as well as the hair follicle 202 in its entirety while leaving intact the stratum corneum 210 that lies superficial to the native tissue that originally surrounded the extracted follicle.

Figure 3:
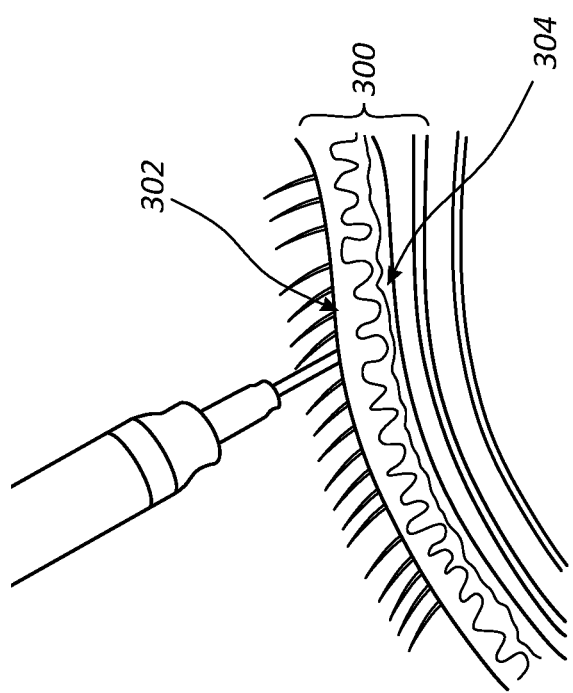
FIG. 3 is a full-thickness cross-section of scalp undergoing preparation for hair restoration surgery.
Figure 4:
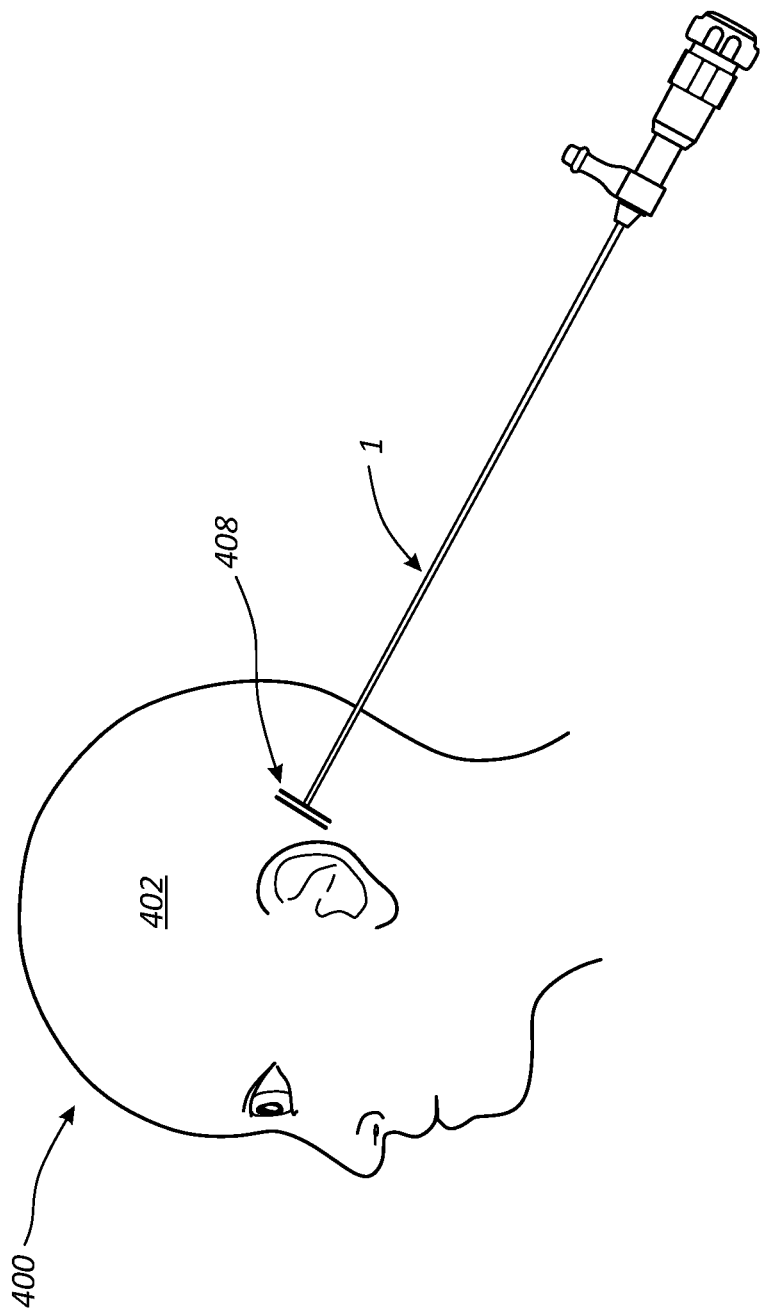
FIG. 4 shows the surgical approach for endoscopic surgical hair restoration.

Referring to FIG. 3, prior to the initiation of hair restoration surgery, sterile saline tumescence (typically about 1-10 mL/cm$^2$) is applied to a scalp 300 at two levels within the area from which hair follicles will be harvested: a first superficial level 302 approximately 2 mm below the skin surface and a second deep level 304 approximately 4-5 mm deep to the skin surface. Together, the tumescent applications at superficial level 302 and deep level 304 facilitate extraction of the follicular bulb from its native surrounding tissue. The first superficial layer of tumescence 302 helps distance the follicle of interest from neighboring follicles and increases skin turgor in patients with otherwise friable tissue. The second tumescent layer 304 distances the dermal papilla 216 from any nearby vascular and nerve plexus deep to the follicle bulbs, thus helping define plane 230 in which a visual cavity can subsequently be created.

Referring to FIGS. 4 and 5A-E, an endoscopic approach to follicular harvesting uses an endoscope 1, also known as a piloscope when related to hair follicle manipulation, to dissect a plane of subcutaneous tissue deep to hair follicles in a scalp 402 of a patient 400. A unilateral full-thickness 1 cm incision 408 is made in a post-auricular zone of scalp 402. A 0.5 mm cannulated metal trocar 8 (e.g. Olympus model A4604 15$_3$) containing a 0.4 mm endoscope 1 (e.g., a model A4605 30° manufactured by Olympus) attached to a thin linear cutting blade 10 is inserted into incision 408 to dissect a plane of sub-follicular subcutaneous tissue (230 of FIG. 2A), creating a layer of separation deep to the follicular bulbs. The layer of separation is, for instance, 1-5 mm deep to the follicular bulbs. In some embodiments, the layer of separation is 1-3 mm deep to the follicular bulbs so as to enable close visual proximity to the follicular bulbs without altering their structural integrity. In general, the depth of the layer of separation is such that an operator of endoscope 1 can visualize and separate connective tissue beneath the plane of the follicular bulbs while minimizing trauma to the blood vessels and nerve vessels in the vicinity.

The layer of separation is converted by humidified insufflation, external traction, or balloon expansion to an enlarged visual cavity in which an operator of endoscope 1 observes the deep structures (e.g., the bulb 214) of each individual follicular unit (FU) in the surgical donor area 106 prior to excising the intact FU from its native surrounding tissue for subsequent transplantation into the surgical recipient area (e.g., regions 102, 110 and 104 of FIG. 1A). Each FU may contain one or more individual hair follicles and can be defined by visualization from below based on the natural-occurring arrangement of the bulb region. An FU may be classified based on its caliber and the quantity of hairs it contains as a single-haired FU, a fine-single-haired FU, a double-haired FU, a fine double-haired FU, a triple-haired FU, or a follicular family containing four or more intact hair follicles.

Figure 5A:
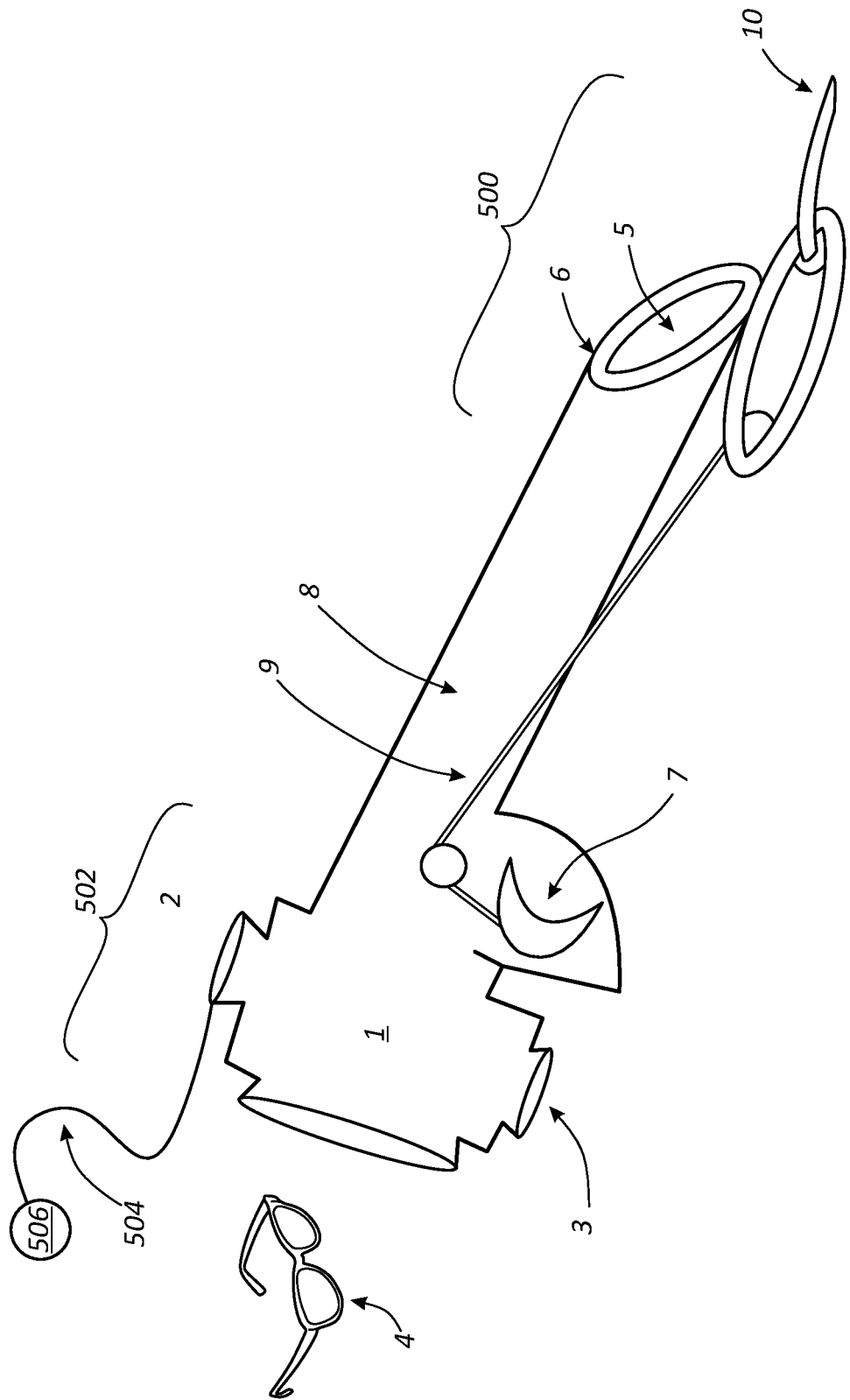
FIG. 5A shows an endoscope including a distal dissection blade attachment.

Referring to FIGS. 5A and 5B, cutting blade 10 is attached to a distal end 500 of endoscope 1 and is manipulated by an operator via a hand-held engagement device (e.g., a trigger) 7 at a proximal end 502 of endoscope 1. Cutting blade 10 is typically about 0.5-6.0 mm in length. Trigger 7 controls cutting blade 10 to move with a rotating motion, facilitating the cutting and separation of soft subcutaneous adipose tissue. When activated, cutting blade 10 advances dissection by pushing forward and downward in a clockwise fashion away from distal end 500 of endoscope 1. In addition to the forward and downward motion that advances cutting blade 10 during dissection, an operating lever including a tape 11, a driver wheel 12, and a steering wheel 130 attached to cutting blade 10 enables a side-to-side sweeping motion of blade 10, which enlarges the plane of dissection. In some embodiments, tape 11 is formed of multiple strips of tape to facilitate the side-to-side sweeping motion of blade 10. Cutting blade 10 is adjustable by the operator of endoscope 1 based on indications presented by the scalp tissue of the patient and the comfort of the operator. The operator of endoscope 1 can control the amount of tissue penetration achieved by each advancement of the endoscope as well as the motion of the cutting blade 10 in the side-to-side, up-and-down, and forwards-backwards directions.

In some embodiments, cutting blade 10 may be replaced by a blunt-ended blade, an electrocautery device, a dispenser of pressurized gas or liquid, a balloon-like expanding device, an enzymatic tissue separator, a laser, or any other device capable of separating the connective tissue along a desired plane.

Referring to FIG. 5A, as with most standard endoscopes (e.g., a rigid hysteroscope), endoscope 1 has three ports. A light port 2 accepts light from a fiberoptic light cable 504 (e.g. a model CLK-3 manufactured by Olympus) to enter endoscope 1 through proximal end 502 of the endoscope. An insufflation port 3 is the entry point for moistened insufflation gas, which facilitates, enhances, and maintains the separation of subcutaneous tissue planes. Both light received through light port 2 and insufflation gas received through insufflation port 3 pass through an outer trocar 8 of endoscope 1 and are emitted in an outer oval 6 at distal end 500 of endoscope 1. An imaging port 4 allows magnified viewing of tissue in the region of distal end 500 through a lens 5 at the beveled distal end 500 of endoscope 1. In some embodiments, an operator looks directly through imaging port 4. In other embodiments, an electronic camera (e.g., a CCD camera) is coupled between imaging port 4 and a television monitor to facilitate viewing.

Because cutting blade 10 is positioned directly below lens 5 and because of the beveled profile of distal end 500, blade 10 as well as the tissue through which it cuts are easily viewed.

A humidified gas such as carbon dioxide is used for insufflation. The temperature of the gas falls between 30-33° C. The pressure of the insufflation gas ranges from 10-50 mm Hg and is determined by the scalp laxity in order to enhance the creation and maintenance of a visual cavity established by cutting blade 10. Together, the blade and insufflation pressure establish a visual cavity with a clearance of at least 1.0 mm. Such a clearance allows for the advancement of 0.4 mm endoscope 1 and outer trocar 8 attached to cutting blade 10.

A light source 506 emitting light at a specific wavelength allows further and deeper visualization and subsequent penetration through the scalp sub-follicular subcutaneous tissue by endoscope 1 while still retaining or improving the ability to selectively visualize hair follicle structure and essential follicle components required for self-renewal (e.g. the stem-cell containing bulb 214 and bulge 212). In some embodiments, to better view essential FU components required for self-renewal in differently-pigmented hair follicles that may be otherwise difficult to visualize, illumination light from light source 506 is filtered prior to being reflected toward the plane of hair follicles by a diatonic mirror positioned either inside or outside of endoscope 1. Exemplary fluorochrome filters include, but are not limited to: FITC (excitation wavelength=490 nm, emission wavelength=525 nm), DAPI (excitation=350 nm, emission=470 nm), or rhodamine (excitation=511 nm, emission=534 nm). When the illumination light has a range of wavelengths, light emitted from the various components of hair follicles is filtered by an appropriate, emission filter positioned prior to imaging port 4.

Visual enhancement of each individual FU within the donor area, or specific areas of the anatomy of each FU, may be achieved using either an extrinsic fluorophore dye or a methylene blue dye applied topically pre-operatively and that is absorbed by the follicles within about 10-15 minutes. In other cases, an antibody may be applied that enables each FU to be visually differentiated from the surrounding tissue. In some embodiments, a bright, minimal-heat emitting external light source (such as a halogen bulb with a dichroic reflector that reduces heat in the light beam by nearly 70% by transmitting the infrared radiation, or heat, backwards) is placed against the outer scalp surface to facilitate visualization of the follicle bulbs beneath the skin surface. In other embodiments, selective visual enhancement is achieved using visual isolation techniques that take advantage of the unique biological structure and/or properties of hair follicles (e.g., absorption or reflection characteristics of light or sound waves or magnetic properties). Often, the specific areas of the hair follicle that are selectively visualized contain the stem cells required for self-renewal of the entire viable structure, enabling an operator of the endoscope to identify and excise the necessary tissue.

Control of any unintentional bleeding created by disturbance to the surrounding vasculature can be achieved with insertion of an electrocautery device (not shown) through the same port in which the endoscope 1 rests. The tip of the electrocautery device can be visualized through the lens 5 at the distal end 500 of the endoscope. Once the active blood vessel is clearly viewed, a range of 6-16 Hz of monopolar electrocautery current can be used to control bleeding. If this is not successful in control of bleeding, direct external pressure can safely be applied by the operator to the patient's scalp once the instruments have been safely removed from beneath the scalp until the bleeding has ceased. In some cases, a liquid dispenser can be attached to endoscope 1 to enable a liquid flush following electrocautery.

Figure 6B:
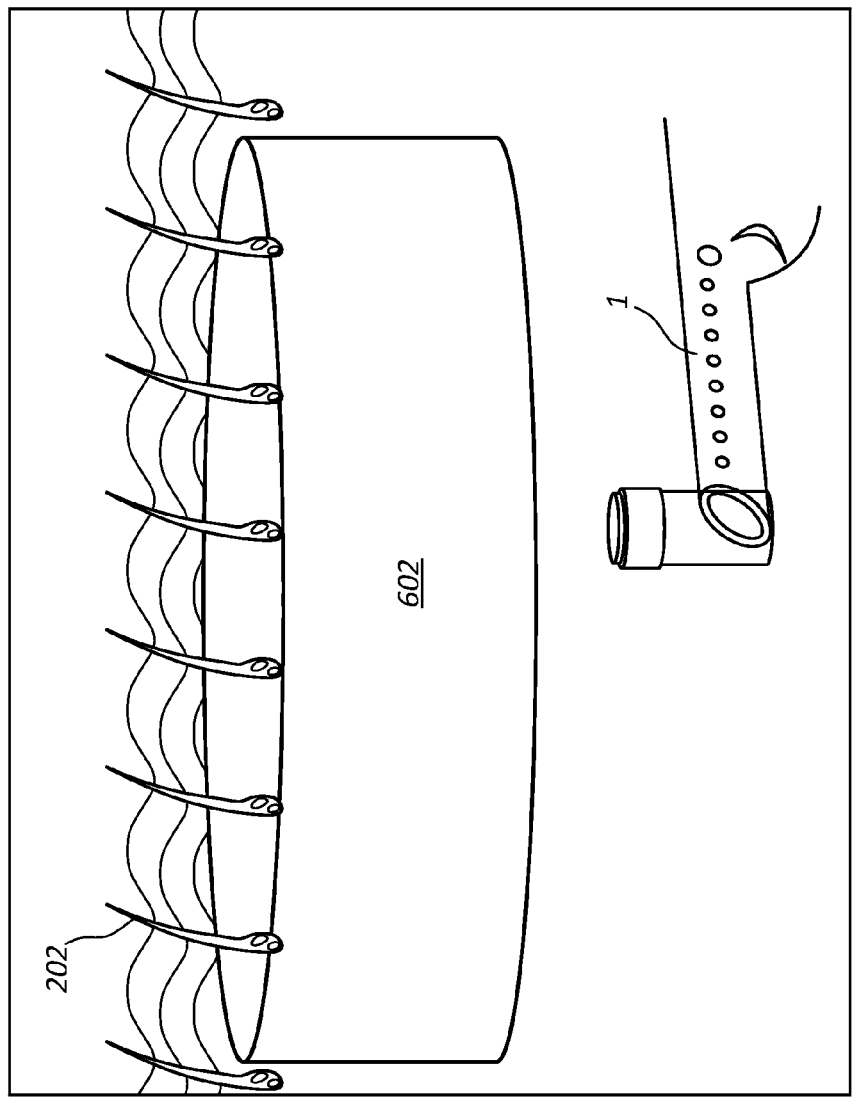
FIG. 6B shows a detailed view of the barrier device of FIG. 6A defining the safe donor area.

Referring to FIGS. 6A-B, once a visual cavity 604 is established by surgical dissection using cutting blade 10, the cavity 604 is maintained by a barrier device 602 in order to maintain ample clearance for the entrance and function of the distal end of endoscope 500 as well as both its attached dissection and extraction modules. The barrier device expands along the established subcutaneous plane 230 to enable the operator to define the outer border of the "safe donor zone," a region of relative donor hair follicle permanence determined pre-operatively by the surgeon on the basis of the patient's medical, surgical, and family history, the caliber and density of the patient's hair, and other physical characteristics. The safe donor zone (often seen in men as a "horseshoe rim" of permanent hair) represents a zone within which FUs will most likely continue to persist and grow throughout a patient's lifetime; outside of this zone, FUs may not be permanent. The use of barrier device 602 to surround the safe donor zone ensures transplantation of permanent FU and prevents the inadvertent extraction of hairs outside this zone. Expansion of the barrier device facilitates identification of individual FU within a region of high hair density in the overlying skin as the inter-follicular skin surface is increased. Visual cavity 604 is kept moist throughout the surgical procedure by periodic administration of saline spray at, for instance, 50-100 mL/hour. Humidified insufflation through insufflation port 3 is preferably performed at least about every 5 minutes.

Referring to FIG. 6C, the barrier device 602 may also be used to expand the surface area of the intact skin above, increasing the distance between adjacent hair follicles 202 (or, in other applications, increasing the distance between each relevant tissue region of interest). The spreading of the skin does not injure the hair follicles or the skin, but rather temporarily increases the natural spacing between adjacent follicles. This spreading facilitates visualization, identification, and classification of the hair follicles from beneath the surface of the skin. The barrier device 602 creates and retains an enlarged visual cavity beneath the surface of the skin while it is in place; once the device is removed, the overlying skin surface area is reduced to its original state. Barrier device 602 may be, for instance, a balloon expander or a gripping device applying force external to the skin. In some embodiments, barrier device 602 is a porous structure positioned beneath or within the skin that allows for various tissues of interest (e.g., hair follicles) to protrude through the device at desired locations in the porous structure of the device.

Referring to FIG. 7, once surgical dissection of the visual cavity is completed and a clearance of at least 1.0 mm is maintained to ensure safe passage of surgical instrumentation, an extraction device 701 is attached to distal end 500 of endoscope 1 and used to isolate, punch, and remove intact hair follicles. In the embodiment depicted, extraction device 701 is a cylindrical punch. However, in other embodiments, the extraction device may be an oval, cuboid, or hooked device, or another device having curved or straight edges and capable of performing the relevant functions. Extraction device 701 contains two concentric cylindrical components: a coring, beveled-edged cylinder 13 used to pierce the adipose and dermal tissue surrounding the bulb of an intact hair follicle 19 (see FIG. 7A); and a clipping cylinder 14 possessing a series of inward-angled levers 704 (see FIGS. 7E-7H) that cut the final epidermal tissue to which the intact follicle remains tethered in order to isolate the follicle from surrounding tissue. In other embodiments, coring cylinder 13 is blunt-edged and presses against the sub-follicular, subcutaneous tissue from below to stabilize the device so that the coring cylinder can engage prior to coring. The clipping cylinder 14 is driven by a lever 15 that can be controlled by the operator via a cable 9 attached to a trigger 7 at the proximal end of the endoscope 1. The axis of the extraction device 701 is generally oriented at an angle to the longitudinal axis of endoscope 1 in order to facilitate flow through the extraction device. Although the extraction device described herein is composed of two concentric components, in other embodiments, extraction device 701 is a single entity. In some embodiments, extraction device 701 and cutting blade 10 are affixed together onto distal end 500 of the endoscope.

An operator of endoscope 1 views follicle 19 in its entirety through visual lens 5 (see FIG. 5A) from within coring cylinder 13. The operator is thus constantly aware that all components important for follicular self-renewal (including the follicular bulb 214, the bulge 212, inner 222 and outer root sheath 224 shown in FIG. 2B) are included in the dissection process.

Figure 8:
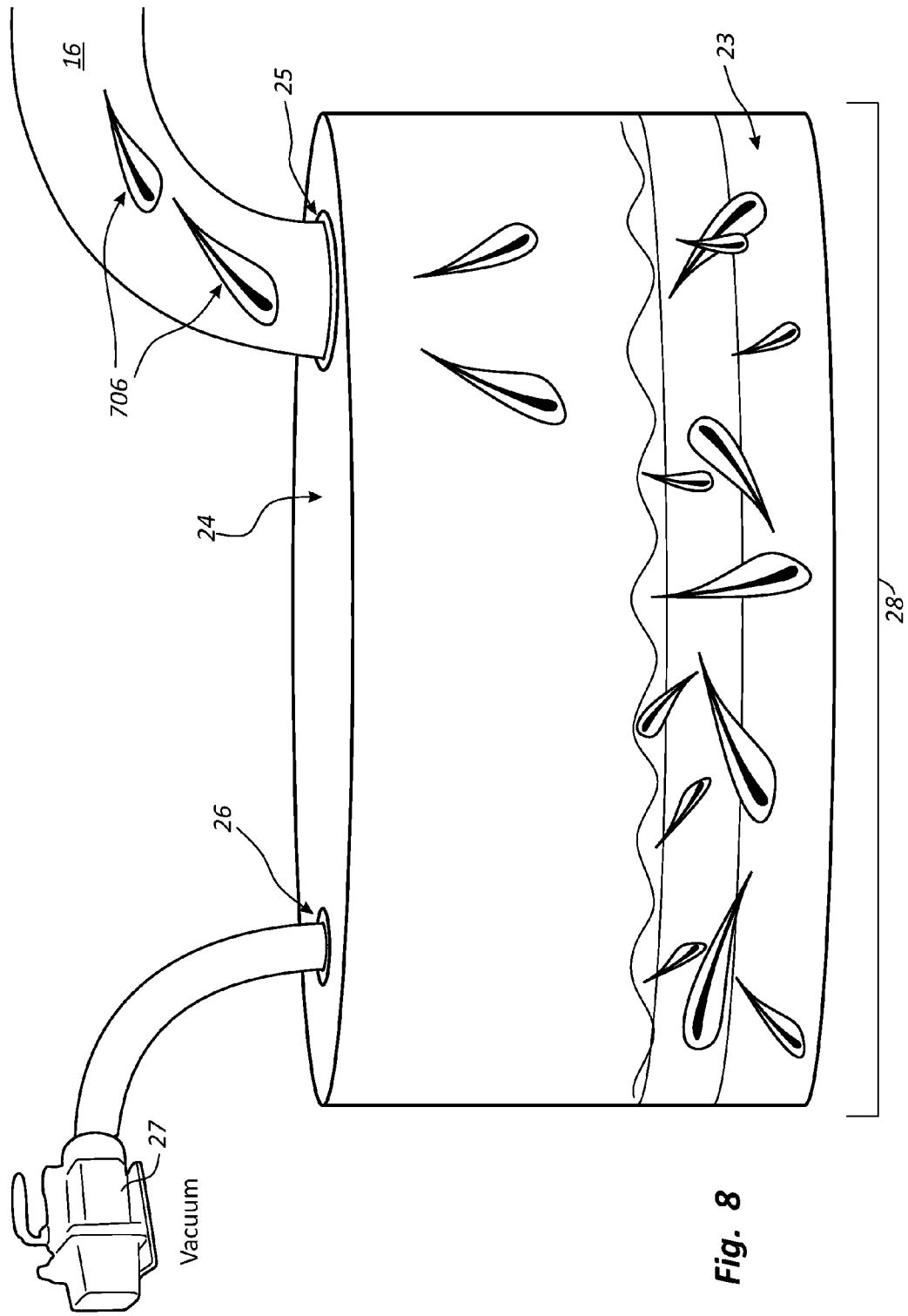
FIG. 8 shows a graft preservation tank.
Figures 9A, 9B, 9C:
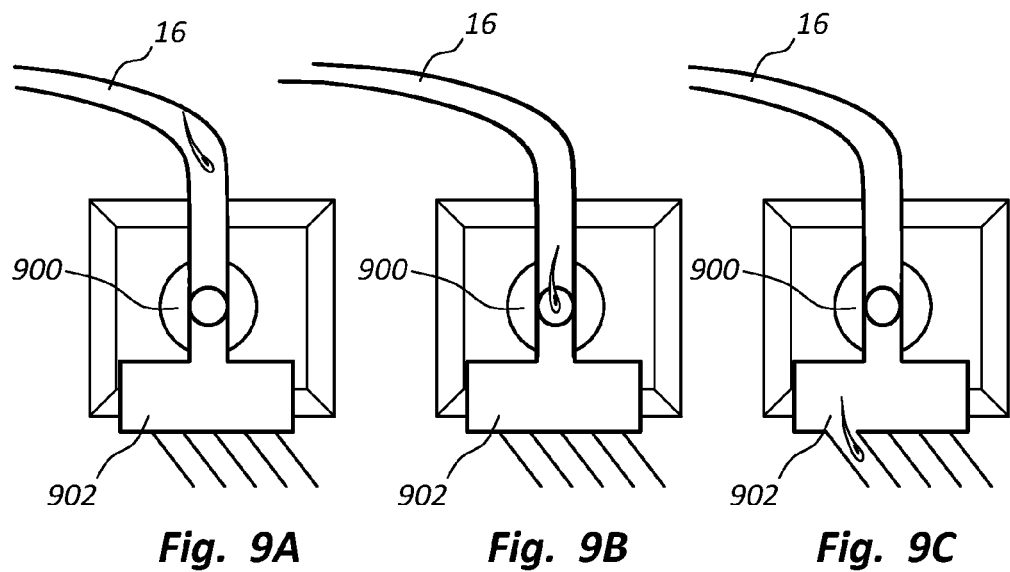
FIGS. 9A-9D illustrate the steps by which extracted follicular units are separated prior to reaching the preservation tank of FIG. 8.
Figure 9D:
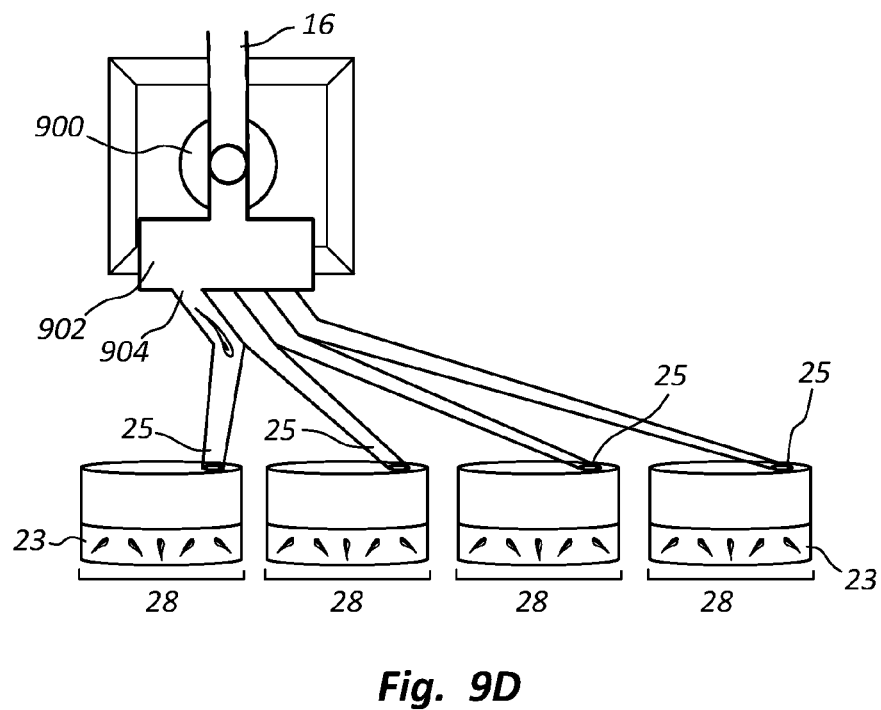

Extraction device 701 is connected to a moistened vacuum suction tubing 16, which is in turn connected to a vacuum source 27 (see FIG. 8). Vacuum source provides suction that flows from above extraction device 701 downward toward vacuum tubing 16. The vacuum effect is readily activated/deactivated and/or increased/decreased by a switch or foot pedal attached to vacuum source 27.

Referring to FIGS. 7 and 7A, coring cylinder 13 attaches to subcutaneous adipose tissue 700 deep to hair follicle 19 using a combination of 1) operator-driven movement upwards controlled at the proximal end of the endoscope, and 2) vacuum suction downwards generated from vacuum tubing 16. The combination of upwards and downwards force creates a tight seal 13A between extraction device 701 and peri-follicular subcutaneous soft tissue 700, thus stabilizing the tissue with respect to endoscope 1 and ensuring proper isolation and subsequent controlled removal of intact hair follicle 19.

Referring to FIG. 7B, once suction seal 13A has been established, the operator presses trigger 7 to engage lever 18 to advance to position 18A while still attached to the base of coring cylinder 13 thus moving coring cylinder 13 upwards in a twisting fashion. The coring cylinder may be twisted either clockwise or counterclockwise as it is moved upwards, provided the direction of rotation is reversed when the extraction device later pulls downwards. A detection device 14A embedded within coring cylinder 13 prevents coring cylinder 13 from piercing stratum corneum 210 or from cutting tissue within a preselected distance (e.g., less than 1 mm, or about 0.74 mm, which is the depth below the surface at which the stem cell containing isthmus begins) of the skin surface 702 as coring cylinder 13 moves upwards. Detection device 14A may be, e.g., at the top of coring cylinder 13, positioned elsewhere within coring cylinder 13, or may be enabled by an innate feedback process based on a gradient of resistance within the skin (described in greater detail below). Studies have demonstrated that the bulge region of the hair follicle (a critical region in which hair stem cells reside) lies an average of 1.66 mm beneath skin surface 702. Therefore, it is critical to surgically create the upper border of the FU of interest 19 between this level of the bulge and the skin surface. Detection device 14A ensures no trauma is inflicted to the stratum corneum so as not to outwardly disrupt its structural integrity as the intact hair follicle 19 is isolated and removed.

Detection device 14A determines the proximity of the coring cylinder 13 to the skin surface 702 based on the physical and structural characteristics of the skin. As the coring cylinder approaches the surface of the skin, the cutting motion is decreased. For instance, if the coring cylinder is cutting using rotational torque, the rotational frequency is lessened as the coring cylinder moves closer to the skin surface because of the increased resistance posed by the increased collagen and fibrin content in the epidermis and the stratum corneum (i.e., following the equation $V=IR$). In some cases, an operator can detect the desired proximity of the cutting device to the stratum corneum via feedback from the detection device 14A and can stop the cutting based on this feedback.

Referring to FIGS. 7C and 7E-7H, when the point of maximum safe coring cylinder 13 piercing upwards towards the skin surface has been achieved, cutting devices 704 atop clipping cylinder 14 are engaged. Cutting devices 704, including multiple inwardly-curved blades, pass inward from a top circumference of clipping cylinder 14 towards the center of the coring cylinder 13 in which the hair shaft lies. The shearing of the superficial layer of epidermis 204 by these curved blades may reach the hair shaft, separating the follicle from its native tissue. A continuous vacuum provided through moistened tubing 16 provides an additional downward force that induces follicle 19 to separate away from its surrounding native environment.

In some embodiments, clipping cylinder 14 is composed of semi-flexible metal (e.g., nitenol) enabling the clipping devices 704 to lie flush along the surface of the coring cylinder 13 when retracted and to resume their inward-angled position once the clipping cylinder is advanced beyond the distal tip of the coring cylinder 13. The downward force from the intact stratum corneum above also helps direct the inward-angled levers further inward, increasing their ability to clip the remaining epidermal tissue.

Once follicle 19 separates from its native tissue, clipping cylinder 14 is reset by trigger 7 at proximal 502 of endoscope 1 in preparation for a subsequent hair follicle removal.

Referring to FIG. 7D, an isolated follicular unit (FU), or micro-graft, 706 including intact hair follicle 19 and any attached peri-follicular tissue is driven into moistened vacuum tubing 16 by a vacuum force 27 (in FIG. 8) and an irrigation jet of sterile saline (for instance, 0.5 mL-1.5 mL of saline) ejected from a saline port 22 near distal end 500 of endoscope 1 when activated by trigger 7.

In an alternative embodiment, coring cylinder 13 is moved upwards by the action of trigger 7. In this case, the cutting devices 704 are positioned on coring cylinder 13 and are engaged when the coring cylinder has reached its maximum safe advancement. Once the upper, superficial border of the to-be-isolated hair follicle 19 has been sufficiently separated by the cutting devices, the operator activates trigger 7 to cause coring cylinder 13 to be pulled downward in a twisting fashion, rotating in the opposite direction from its rotation upon upward movement. Microscopic, one-way, gripping ledges (akin to hooks) protruding from within coring cylinder 13 grasp the peri-follicular tissue 208, 206, and 204 (or 700 as depicted in FIG. 7A) that surrounds hair follicle 19 as coring cylinder 13 is pulled downward, rotating in the opposite direction from its rotation upon upward movement. The gripping and tugging motion of the microscopic ledges within the cylinder coupled with curved blades 704 that rest atop, or superficial to, the soon-to-be isolated hair follicle 19 provide mechanical pressure to pull the follicle 19 out of its native, soft-tissue environment.

Although the cutting devices 704 are described above as sharp blades, other variations are also possible, including a rotational blade or lever, a laser, an enzymatic solution, or another type of cutting device appropriate to the surgical situation.

Referring to FIGS. 9A-9D, micro-graft 706 including the isolated intact hair follicle 19 is dragged through moistened suction tubing 16, through an entrance port 25, and towards an isolation container 28. Multiple isolation containers 28 are used, each accepting a different category of FU (e.g., determined based on the number and/or caliber of intact hair follicles contained in the FU). In order to separate the FUs into the appropriate isolation containers, a sensor 900 positioned along tubing 16 identifies and categorizes each FU based on the number and caliber of intact hair follicles it contains. Note that in the context of this disclosure, an intact hair follicle is defined as a hair follicle that contains sufficient amounts of both stem cell containing regions (i.e., the bulb (dermal papilla) and the bulge region (within the isthmus) that are required for hair follicle self-renewal). The structural connection between the bulb and the bulge within a follicle must be in communication for the follicle to be considered intact.

Sensor 900 activates a separation device 902, triggering the opening of a gate 904 corresponding to the appropriate isolation container 28 and allowing the FU to reach its appropriate isolation container. The separation is activated by a suction force that is greatest along the path toward the selected isolation container.

Referring to FIG. 8, each isolation container 28 contains a sterile collection pool 23 of preservation solution (e.g., normal saline, oxygen- and ATP-enriched solution, etc.) chilled to a temperature range of 1-10° Centigrade. The collection pool is similar to the Schuco® Suction Canister and the vacuum source 27 used to generate suction pressure is akin to Schuco® Vac. Vacuum source 27 provides the vacuum used to help isolate intact to FU 706, as described above. The vacuum pressure ranges from 50-300 mm Hg. A filter 26 positioned between vacuum source 27 and isolation container 28 maintains the sterility of collection pool 23. A barrier 24 (typically about 2 cm in height) located near entrance port 25 helps to ensure that grafts 706 drop downwards into collection pool 23 rather than being pulled toward vacuum source 27.

The collection of isolated micro-grafts 706 contained in pool 23 of preserving solution is subsequently separated further manually based on follicle characteristics such as number of hairs per FU and/or caliber of each individual hair. Each FU bundle 706 is sent to one of the following collection troughs: fine, single-haired FU; coarse, single-haired FU; fine, two-haired FU; coarse, two-haired FU; fine, three-haired FU; coarse, three-haired FU; and follicular families (FF) containing clusters of more than three hairs per FU.

After the desired number of intact FU have been effectively removed from the patient, the barrier device, endoscope 1, extraction device 701, and visual trocar 8 in which they are contained are removed from the visual cavity beneath the patient's scalp. Afterwards, the 1 cm incision into which the endoscope and its attachments were introduced is sutured closed using 5-0 nylon sutures in a continuous running suture so as to leave a nearly imperceptible linear scar in a hidden post-auricular zone.

Coincident with the endoscopic removal of FU, recipient sites in the patient's scalp are created with ordinary hypodermic needles ranging from 16-25 gauge.

In general, the above-described surgical removal process takes place as the patient lies either upright, on one side, prone, or supine on a surgical table that allows access to the donor area. Prior to the start of the procedure, the patient is given appropriate anti-anxiolytic and analgesic medication to ensure comfort throughout the follicle removal process. In addition, a small dose (e.g., 1-3 mL) of local anesthetic may be used at the port of entry in which the initial incision is made and at which closing sutures are ultimately placed.

In some embodiments, FUs may be removed by an enzymatic and/or laser-based approach from within the visual cavity rather than by the cutting approach described above.

In many cases, the endoscope described above also includes additional features including, but not limited to, saline flush capability, electrocautery capability, staple and/or sutering capability, and a provision for lens cleaning.

Although the devices and methods described above are controlled by an operator, robotic or otherwise automatic control of the endoscope is also within the scope of the disclosure.

In an alternative embodiment, a miniaturized version of the endoscope described above may be used for the removal of body hair, e.g., by ablating or killing the hair follicles below the skin surface using methods such as lasers, cautery, heat, electric current, enzymes, or an extraction device.

Although the above-described surgical technique was depicted with respect to the removal of hair follicles, it is to be understood that the technique is broadly applicable and may be used for other surgical applications. The foregoing description is intended to illustrate and not to limit the scope of the invention, which is defined by the scope of the appended claims. Other embodiments are within the scope of the following claims.

What is claimed is:

1. A surgical apparatus for removing a target region of a tissue from a surrounding tissue by approaching the target region from below and through a subcutaneous layer, comprising:
    an elongated member configured to approach the target region from below, the elongated member including a first end and a second end;
    a dissection module removably attachable to the first end of the elongated member, the dissection module including a tissue separating device configured to dissect a plane of the subcutaneous layer; and
    an extraction module configured to approach the target region from below, the extraction module being removably attachable to the first end of the elongated member, the extraction module including:
        a suction port;
        a tissue removal implement disposed within the suction port, the tissue removal implement including a coring cylinder; and,
    an imaging system configured to view the target region from below and from within the coring cylinder.

2. The surgical apparatus of claim 1, wherein the elongated member accepts the dissection module and the extraction module interchangeably.

3. The surgical apparatus of claim 1, wherein the imaging system is attached to a second end of the elongated member, the imaging system including:
    a light source for illuminating a target through a hollow passage in the elongated member between the first end and the second end; and
    a viewing port for receiving an image of the target.

4. The surgical apparatus of claim 1, wherein the tissue removal implement is disposed concentrically within the suction port.

5. The surgical apparatus of claim 1, wherein the coring cylinder is configured to separate the target region of the tissue from the surrounding tissue.

6. The surgical apparatus of claim 1, wherein the tissue removal implement further comprises a clipping cylinder.

7. The surgical apparatus of claim 6, wherein the clipping cylinder further comprises a circumference and at least one cutting device configured to provide a shearing action inward from the circumference.

8. The surgical apparatus of claim 6, wherein the clipping cylinder further comprises at least one cutting device that includes at least one of blades, arms, levers, chemicals, enzymes, and lasers.

9. The surgical apparatus of claim 6, wherein the clipping cylinder is disposed concentrically around the coring cylinder.

10. The surgical apparatus of claim 1, wherein the coring cylinder includes a plurality of gripping ledges configured to grasp the target region, the gripping ledges being disposed on an inner surface of the coring cylinder.

11. The surgical apparatus of claim 1, wherein the suction port is oriented at an angle to a longitudinal axis of the elongated member.

12. The surgical apparatus of claim 1, wherein the elongated member includes a control mechanism connectable to at least one of the tissue separating device and the tissue removal implement.

13. The surgical apparatus of claim 1, wherein the tissue separating device includes a blade that is configured to move relative to the elongated member.

14. The surgical apparatus of claim 1, wherein the extraction module further comprises a detection device configured to determine a proximity of the coring cylinder to a surface of the skin.

15. The surgical apparatus of claim 14, wherein the detection device further comprises a sensor configured to detect a characteristic of the skin as the extraction device approaches the skin from below the skin.

16. The surgical apparatus of claim 1, wherein the elongated member is flexible.

17. The surgical apparatus of claim 1, wherein the tissue separating device includes at least one of a blade, a balloon, an electrocautery device, a device that dispenses at least one of a pressurized gas and a liquid, an enzymatic tissue separator, a chemical tissue separator, and a laser.

18. The surgical apparatus of claim 1, wherein the suction port is in fluid communication with a reservoir that receives the target region of the tissue extracted by the tissue removal implement.

19. The surgical apparatus of claim 1, wherein the extraction module includes an axis that is configured to be oriented relative to a longitudinal axis of the elongated member.

20. An endoscopic surgery kit for use with at least one endoscope, the endoscopic surgery kit comprising:
a dissection device for dissecting a cavity below the skin of a patient, comprising:
a first elongated member; and
a tissue separating device attached to a first end of the first elongated member; and
an extraction device for insertion into the cavity, comprising:
a second elongated member;
a suction port attached to a first end of the second elongated member; and
a tissue removal implement configured to approach a target region of a tissue from below and to remove the target region of the tissue from a surrounding tissue, the tissue removal implement disposed within the suction port, the tissue removal implement including a coring cylinder; and
an imaging system configured to view the target region from within the coring cylinder.

21. The endoscopic surgery kit of claim 20, wherein the dissection device further comprises another imaging system positioned at a second end of the first elongated member.

22. The endoscopic surgery kit of claim 20, wherein the imaging system includes:
a light source for illuminating the target region located at the first end of the second elongated member through a hollow passage in the second elongated member; and
a viewing port for receiving an image of the target region.

23. A method for removing a selected portion of a skin tissue from a surrounding tissue by approaching the skin tissue from below a surface of the skin, comprising:
using a tissue separating device attached to an end of an elongated member to create a cavity below the skin of the patient; and
from within the cavity, performing the steps of:
viewing with an imaging system the selected portion of the skin tissue from below the selected portion and from within a coring cylinder of a tissue removal device;
approaching the selected portion of the skin tissue from below the selected portion;
applying suction to the selected portion of the skin tissue via a suction port attached to the end of the elongated member;
isolating the selected portion of skin tissue from a surrounding tissue using the coring cylinder; and
applying a downward force to the selected portion of skin tissue using the tissue removal implement to extract the selected portion of skin tissue from the surrounding tissue without altering an outward appearance of the skin.

24. The method of claim 23, wherein the selected portion of skin tissue includes a hair follicle and creating a cavity below the skin includes creating a cavity in a plane below the hair follicle.

* * * * *